United States Patent [19]

Woodson et al.

[11] Patent Number: 5,609,613
[45] Date of Patent: Mar. 11, 1997

[54] CONTROL OF PACING RATE IN DUAL-CHAMBER, RATE-ADAPTIVE PACEMAKERS

[75] Inventors: Drury Woodson; Michael Lee; Joseph Vandegriff, all of Angleton, Tex.; Eckhard Alt, Ottobrunn, Germany; Lawrence J. Stotts, Angleton, Tex.

[73] Assignee: Intermedics, Inc., Angleton, Tex.

[21] Appl. No.: 433,788

[22] Filed: May 3, 1995

[51] Int. Cl.$^6$ ........................................ A61N 1/00
[52] U.S. Cl. .................................................. 607/19
[58] Field of Search ............................ 607/19, 9, 20, 607/17

[56] References Cited

U.S. PATENT DOCUMENTS

| | | |
|---|---|---|
| 4,140,132 | 2/1979 | Dahl . |
| 4,228,803 | 10/1980 | Rickards . |
| 4,312,355 | 1/1982 | Funke . |
| 4,363,325 | 12/1982 | Roline . |
| 4,421,116 | 12/1983 | Markowitz . |
| 4,432,362 | 2/1984 | Leckrone . |
| 4,945,909 | 8/1990 | Fearnot et al. ........................ 607/19 |

Primary Examiner—Marvin M. Lateef
Assistant Examiner—Scott M. Getzow
Attorney, Agent, or Firm—Wigman, Cohen, Leitner & Myers, P.C.

[57] ABSTRACT

A programmable dual-chamber artificial cardiac pacemaker senses atrial activity and normally tracks the sensed atrial activity in pacing the ventricular activity. An accelerometer located in the case of the pulse generator portion senses physical exercise by a patient when the pacemaker is implanted in the patient, and generates a rate control signal indicative of extent of the sensed physical exercise. The pulse generator is programmed for ventricular pacing rate control in multiple rate zones bounded by rate limits including a ventricular tracking limit (VTL) that varies dynamically with sensed physical exercise and a higher mode switch rate. The ventricular pacing rate tracks the sensed atrial activity on a 1:1 basis for atrial rates below the dynamic VTL (DVTL) during a predetermined interval of time for which the DVTL applies, and tracks the sensed atrial activity in Wenckebach behavior for atrial rates above the DVTL up to the mode switch rate with the ventricular pacing rate limited by the DVTL. The mode switch rate is set to effect a switch from dual-chamber to single-chamber mode when the sensed rate of atrial activity exceeds the mode switch rate for a programmed number of cardiac cycles, in which the ventricular pacing rate is controlled solely by sensed spontaneous ventricular activity without regard to the DVTL or sensed physical exercise. The mode switch rate also effects a reversion to the dual-chamber mode when the sensed rate of atrial activity drops below the mode switch rate for a programmed number of cardiac cycles, in which the ventricular pacing rate is controlled according to the respective one of the multiple rate zones in which the atrial activity rate is present.

12 Claims, 4 Drawing Sheets

CONTROL OF PACING RATE IN DUAL-CHAMBER, RATE-ADAPTIVE PACEMAKERS

BACKGROUND OF THE INVENTION

The present invention relates generally to artificial cardiac pacing, and more particularly to improvements in the control of ventricular pacing rates of a dual-chamber pacemaker for various conditions of patient rest, exercise/activity, and atrial dysrhythmia, and with the advantage of automatic mode switching between dual-chamber and single-chamber modes.

In general, dual-chamber pacemakers are designed to maintain atrioventricular (AV) synchrony when implanted in a patient. Two electrodes are used, one for sensing atrial signals and the other for stimulating an appropriate ventricular response. A slight delay is imposed between the ventricular response and the atrial signal that prompted it, to correspond to the normal AV delay of about 150 milliseconds (ms).

With the introduction in the late 1970s and early 1980s of fully automatic DDD pacemakers (three-position ICHD code, and related five-position code adopted by NASPE and other pacing organizations, DDD being indicative of sensing and pacing in both chambers and dual chamber response to a sensed beat), several clinical aims were achievable. Among these aims, the devices permitted adapting the pacing rate of the ventricle to depend on the rate of the sensed intrinsic atrial signal, and the AV synchrony. However, as many as 50% of the patients who had DDD pacemakers implanted experienced problems with atrial sensing or with atrial instability in the presence of underlying atrial rhythm disorders. For that patient population, it was necessary to switch from a DDD pacing mode back to a simple VVI pacing mode (a ventricular demand mode, in which ventricular pacing is inhibited by spontaneous electrical activation of the ventricle).

Despite the development of significant technological improvements over the early dual-chamber pacemakers, in such things as sense amplifiers, electrodes for atrial leads, and timing cycles including dynamic AV delay and refractory periods, a considerable percentage of patients with dual-chamber pacemakers still suffer from inadequate atrial rates. Underlying disease is the primary culprit, with estimates that about one-third of all patients with sick sinus syndrome (characterized by sinoatrial (SA) arrest or SA exit block) have inappropriately high atrial rates accompanying atrial fibrillation, atrial flutter, or sinus tachycardias including atrial reentry tachycardias and ectopic tachycardiac events (developing from a focus other than the SA node), as well as the slow heart rates that call for bradycardia pacing.

In the past, the most widely used proposal to eliminate problems of inappropriate atrial rate in patients with dual-chamber pacemakers was to establish rate criteria to discriminate between physiologic atrial rates and pathologic atrial rates. For example, a high atrial rate evidenced by the atrial beats exceeding a prescribed number over a specified time interval, could be used for switching the pacing mode from, say, an atrial-sensing, ventricular-tracking DDD or VDD mode to a pure ventricular stimulation mode such as VVI or VVI-R (i.e., VVI with rate responsiveness). In the VVI mode, the sensing and pacing functions are active in the ventricle only, so that in the absence of sensed depolarizations within a preset period, the pacemaker generator generates stimulating pulses at a preprogrammed nominal rate (programmed pacing rate); and if spontaneous depolarizations are sensed at a rate faster than the programmed pacing, the stimulation pulse is inhibited.

But mode switching based on such criteria has produced its own set of problems. If the atrial detection rate is set too low, even physiologically-increased atrial rates following physical exercise can cause the system to revert to an inappropriately low rate. If the criterion for detection of inappropriately high atrial rate is set too high, atrial rates occurring with even slow atrial flutter, sinus tachycardia, or ectopic beats may be below the threshold and cause inappropriately high ventricular pacing rates although the patient may be at rest.

It is essential that the dual-chamber device should respond to inappropriate high atrial rate in a manner that precludes pacing the ventricle at an equally fast rate. The maximum pacing rate (MPR) or upper rate limit of the pacemaker is usually programmed to produce an abrupt 2:1 block, which has its own problems. The total atrial refractory period (TARP, which is the sum of the AV interval and the post-ventricular atrial refractory period or PVARP) affects the upper rate limit in that an atrial rate is reached at which no further sensing of atrial beats can occur because they fall in the atrial refractory period. An abrupt 2:1 block, which can occur even in situations where the high atrial rate may be appropriate because of patient exercise and metabolic need, causes an undesirable abrupt change in the patient's cardiac output and blood pressure.

Wenckebach behavior, a progressive lengthening of the P-R interval such that eventually a ventricular beat does not follow an atrial beat, may be developed at the upper rate limit as a means for slowing the paced rate. Some dual-chamber pacemakers are programmable to allow a more gradual reduction in the patient's heart rate when the atrial rate reaches the 2:1 block imposed by the programmed upper rate limit.

A second approach to solving the problem of intermittent high atrial rate is based on sensing the activity or state of exercise of the patient. A rate-adaptive or rate-responsive pacemaker controls the pacing rate based on the output signal of a sensor such as an accelerometer, a temperature-detecting element, a QT-interval detector, or a detector of impedance-derived minute ventilation.

In addition to use for controlling heart rate, activity sensor-based techniques can be used to monitor the pacemaker's stimulation rate or the patient's intrinsic heart rate. For example, the RELAY™ dual-chamber, multiprogrammable, rate-responsive cardiac pulse generator manufactured by Intermedics, Inc. (Angleton, Tex.) controls the pacing rate and also monitors the adequacy of atrial-triggered stimulation in the atrium.

Where intermittent rhythm disorders such as atrial fibrillation and atrial flutter cause an inappropriately high atrial rate in the normal, unaided heart, the inability for rapid transfer of the electrical signal through the AV node from the SA node causes the ventricle to be stimulated only every other or even every third atrial beat. This self-correction does not occur with the DDD pacemaker because the device itself senses the high atrial rate and accordingly can pace the ventricle at an inappropriately high rate.

However, the MPR of the pacemaker is programmed in a range (typically, from 150 to 170 bpm) to prevent a dangerously high ventricular response. Still, pacing at the MPR is unacceptable at any time that the patient is inactive. Because of high myocardial oxygen consumption, particularly in the presence of existing coronary stenosis, the patient tends to develop symptoms of cardiac insufficiency, lung congestion, shortness of breath, and angina pectoris.

In some prior art dual-chamber, rate-responsive pacemaker generators, the MPR is supplemented by a lesser interim rate which is greater than the lower rate limit of the device—a ventricular tracking limit (VTL) to which the pacing rate moves from its base rate conditioned on a high atrial sensed rate without patient exercise. This conditional VTL (CVTL) was originally incorporated in a temperature sensing, rate-responsive pacemaker developed in the mid-1980s. A simple algorithm that discriminated between patient rest and exercise based on venous blood temperature was used to control a change in rate to a fixed rate that exceeded the lower rate limit of the device by about 30 bpm.

The RELAY™ pacing system uses an accelerometer as a body motion/ activity sensor, and has a CVTL feature which, when programmed "on" (i.e., as an operating condition of the device), undergoes a controlled jump to the CVTL rate when a high atrial rate is sensed without confirmation of patient exercise from the accelerometer. This is considerably less traumatic to the patient than an abrupt move to the MPR. The CVTL is overridden, so long as the MPR is programmed "on", whenever the rate calculated in response to patient exercise exceeds the programmed base pacing rate by a preselected amount—20 bpm, for example. At this exercise (activity) sensor-calculated rate threshold, the pacemaker generator restores the 1:1 AV synchrony up to the MPR. When the sensed atrial rate drops below the activity-calculated rate, the generator performs rate-responsive AV sequential pacing.

The advantage of a CVTL is somewhat moderated by the fact that if an episode of atrial tachyarrhythmia is experienced by the patient during moderate exercise, such as even slow walking, an abrupt rate change can take place from the base rate or current activity-based rate to the MPR of the device. The opposite situation can result when a patient ceases activity—an abrupt drop in rate may occur from the MPR to the CVTL rate. Clearly, this would be undesirable.

Despite the advance in pacing comfort attributable to the CVTL, it would be desirable to further compensate a designated upper rate limit according to changes in the metabolic need of the patient. It is a principal aim of the present invention to provide a rate-responsive, dual chamber pacemaker in which the VTL is implemented to be a dynamic rather than a fixed rate, to minister further to the patient's physiology.

A further object of the invention is to provide a method and apparatus to control the rate at which the ventricle is paced by a dual-chamber pacemaker through several different rate zones, based upon a combination of (i) a dynamic adjustment of the ventricular tracking limit according to an activity signal, and (ii) an automatic mode switch that causes the pacemaker generator to go from a dual-chamber to a single-chamber mode, and to revert to the dual-chamber mode based on an atrial cut-off rate and a programmable rate criterion.

SUMMARY OF THE INVENTION

The present invention, in one exemplary embodiment, encompasses a cardiac pacemaker that enables sensing the patient's metabolic needs coupled with the provision of an operational VTL that is automatically adaptive to those needs by dynamic adjustment to assure that requirements for greater or lesser cardiac output are met in a relatively smooth, timely manner in one of what may be multiple rate zones depending on the particular embodiment. A particular zone extends from an operating VTL defined by the patient at rest, i.e., with no sensor exercise signal, to the MPR. Preferably, the sensor is an accelerometer, and no sensor activity (no physical activity of the patient) produces a VTL at rest (VTLAR).

The dynamic ventricular tracking limit (DVTL) provides an operational VTL that, at any given point, lies between the VTLAR and the MPR of the device. The dynamic adjustment of the VTL between these two rate limits may be based on acceleration, i.e., on physical activity of the patient that translates into sensor acceleration, or sensor activity. The adjustment is calculated during each pacing cycle, and only one operating VTL exists at any given instant of time. The activity or exercise status of the patient may be determined using any known type of activity or exercise sensor, although the accelerometer is the preferred type for reasons of simplicity, capability to be incorporated within the pacemaker generator enclosure, speed of response, sensitivity, and accuracy.

The utilization of a DVTL in a dual-chamber pacemaker represents an important application of the invention in and of itself, in one of its aspects. Rather than relying on a single, fixed VTL—a conditional VTL (CVTL)—as in pacemakers of the prior art, the VTL is continuously adjusted according to sensor activity, at least over a part of a rate range or zone of the pacemaker's operation. In an exemplary embodiment, the DVTL adjusts the VTL between the VTLAR and the MPR based on acceleration. This allows the pacemaker to respond more closely to the hemodynamic needs of the patient at any given time.

The DVTL may be calculated, for example, to correspond to a time interval offset from the calculated pacing rate, with progressive shortening of the interval from the time the patient commences activity and increases activity, and progressive lengthening of the interval as the activity becomes less strenuous and ultimately ceases, within programmed operating VTL rate limits. For example, when exercise commences and increases as detected by the accelerometer, the interval may be shortened by one millisecond (ms) for each X ms shortening of the calculated rate relative to the pacing rate, where X is a variable related to a DVTL rate limiting parameter. Conversely, when the calculated rate drops with cessation of exercise, the interval may increased by Y ms each pacing cycle, where Y is a variable related to a DVTL rate decay parameter. The operating VTL becomes the maximum of (1) the calculated DVTL based on rate limiting and rate decay factors and (2) the calculated pacing rate, up to the absolute limit imposed by the MPR.

Automatic mode switching is another important aspect of the invention to achieve pacing rate control that more closely parallels the patient's true requirements for cardiac output regardless of intermittent atrial dysrhythmia. For this purpose, a mode switch rate (MSR) is designated—above the MPR—that represents an atrial rate unlikely to be exceeded by even a healthy person with a normal cardiovascular system. In an exemplary embodiment, the MSR is set at 220 bpm. The MSR, MPR, and VTLAR are independently programmable, although in the preferred embodiment of the invention VTLAR≦MPR≦MSR.

Mode switching from a dual-chamber mode (e.g., DDD or DDD-R) to a single-chamber mode (e.g., VVI or VVI-R) is set to occur whenever a predetermined criteria of atrial rate over a time interval is met. In the preferred embodiment, the mode switch from DDD-R to VVI-R takes place when the sensed atrial rate exceeds the MSR for a programmed number of consecutive cardiac cycles ranging, for example, from one to seven; and a mode switch for reversion back to dual-chamber mode occurs when the sensed atrial rate falls below the MSR for one cycle.

According to a principal feature of the invention, the ventricle is paced in a different way in multiple rate zones, the boundaries of which are established by programming specified rates and rate limits. In certain zones the paced ventricular rate tracks the sensed atrial rate, albeit in somewhat different ways for different zones—including reliance on the DVTL; and in another zone or zones the device undergoes a mode switch to cause sensing and pacing in the ventricle only, until a mode reversion is effected.

Thus, the combination of the DVTL and mode switching features produces the multiple rate zones, which, in the preferred embodiment, may be viewed as consisting of either three or four different zones. In a three-zone analysis, normal tracking of the paced ventricular rate to the sensed atrial activity takes place in a first zone extending from the programmed pacing rate (PPR) to the operating VTL established by the DVTL; Wenckebach tracking takes place in a second zone extending from the DVTL to the programmed MSR; and mode switching takes place at rates determined by the MSR boundary of a third zone—in which, when the mode switch cycle criterion is met at a rate exceeding the MSR, the device switches to a programmed single-chamber mode, and when the rate drops below the MSR the device reverts to the dual-chamber mode.

In a four-zone analysis, the first zone extends from the PPR to the VTLAR in which sensed atrial activity is always tracked in the ventricle on a 1:1 basis; the second zone extends from the VTLAR to the MPR, in which atrial activity is possibly tracked on either of two different bases depending on physical activity levels; a third zone extends from the MPR to the MSR, in which the pacing rate is Wenckebach-tracked limited by the DVTL; and the fourth zone includes all rates above the MSR. The three-zone analysis would correspond to the four-zone analysis if the third zone of the latter were programmed away by setting the MPR equal to the MSR.

Therefore, a more specific aim of the invention is to provide a ventricular pacing rate control system for dual-chamber pacemakers in which rate regulation is provided differently in different ones of multiple rate zones that are established by programming of the device, together with features of a dynamic VTL and automatic mode switching, to track ventricular response to appropriate atrial rates and sensed physical activity (or exercise), and to cease tracking in the ventricle when atrial rates are inappropriately high attributable, for example, to episodes of atrial flutter, fibrillation, or sinus tachycardia.

BRIEF DESCRIPTION OF THE DRAWINGS

The above and other aims, objects, features and attendant advantages of the invention will become apparent from a consideration of the following detailed description of the presently-contemplated best mode of practicing the invention with reference to certain preferred methods and embodiments thereof, taken in conjunction with the accompanying drawings, in which.

DETAILED DESCRIPTION OF THE PREFERRED METHODS AND EMBODIMENTS

Figure 1:
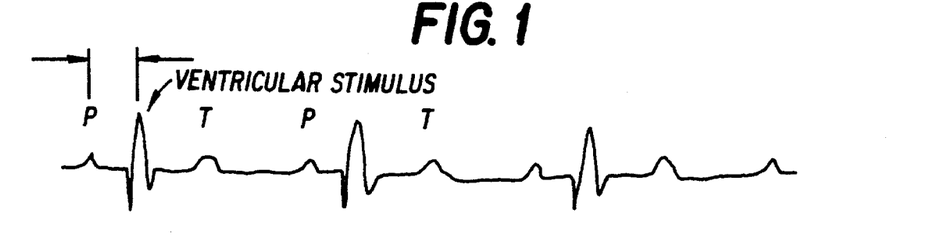
FIG. 1 is a simplified chart illustrating an atrial sense event followed by a ventricular stimulus in the cardiac cycle of a patient's heart.

The atrium is continuously sensed in a dual-chamber pacemaker. As shown in FIG. 1, an atrial sense event such as a P-wave triggers a ventricular stimulus, if no ventricular intrinsic beat is sensed during the A-V interval. This behavior occurs for atrial-sensed events between the lower rate limit (typically 60 bpm) and the upper rate limit (typically 150 bpm) of the pacemaker.

Figure 2:
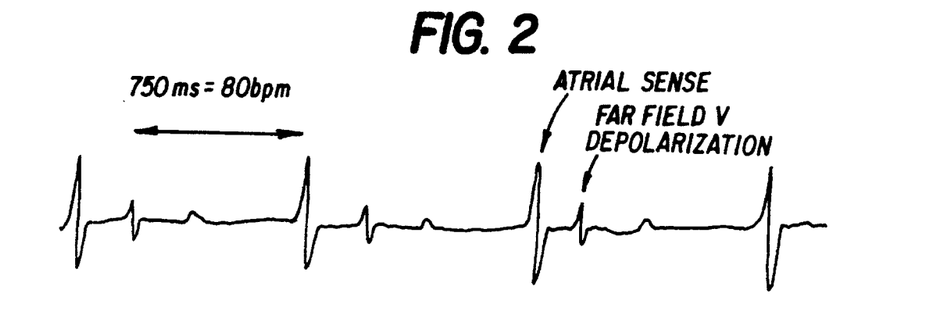
FIG. 2 is a simplified intracardiac electrogram (ECG) illustrating an atrial sense event followed by a far field ventricular depolarization from an atrial signal with sinus rhythm as detected by an atrial electrode.

FIG. 2 shows the atrial amplitude as observed from an atrial lead attached to the myocardium of the atrium. Each of the atrial-sensed events represent a distinct signal with an amplitude on average of about 3 millivolts (mv), while the far field sensing of the ventricular depolarization is considerably smaller. The possibility of over-sensing and double sensing is avoided by the atrial refractory period following a sensed event and by adjusting the atrial sensitivity to a level that eliminates far field ventricular sensing.

Figure 3:
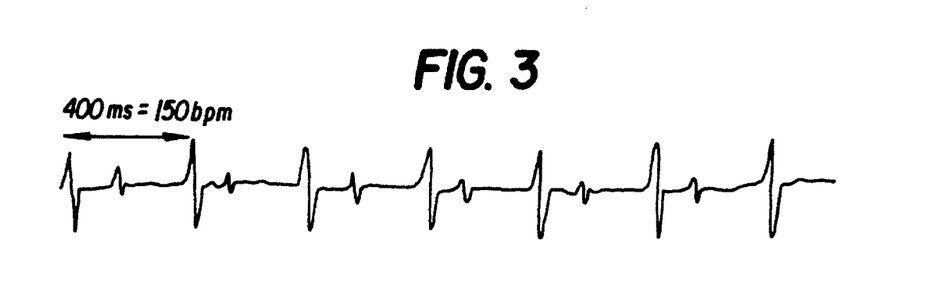
FIG. 3 is a simplified ECG illustrating an atrial sense event similar to that of FIG. 2, except that the detected atrial signal exhibits atrial flutter.

In FIG. 3, the atrial signals represent a slow atrial flutter or inappropriate atrial tachycardia. Here, the atrial rate increases to 150 bpm, for example. The amplitude of the atrial signal is smaller than that detected with the pure P-wave sinus rhythm (FIG. 2), but is still sufficiently large to be sensed by the atrial sense amplifier of the device. A ventricular stimulation will occur following each high-rate atrial sense signal, as long as the atrial rate is within the boundaries of the upper rate limit (i.e., the MPR).

Figure 4:
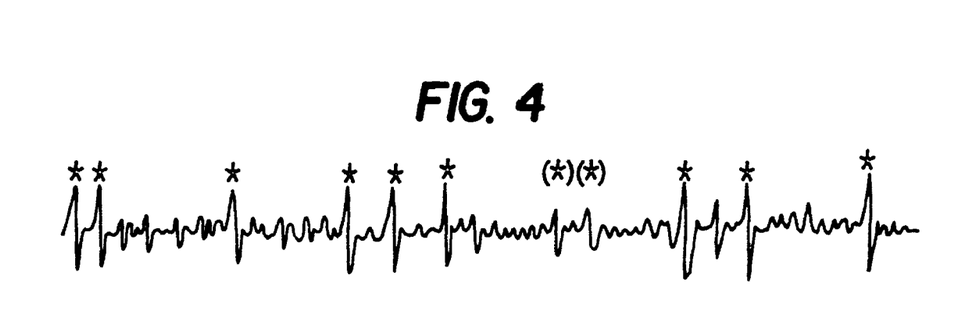
FIG. 4 illustrates the ECG signal for intra-atrial sensing from an atrial lead during atrial fibrillation.

FIG. 4 illustrates the ECG signal for intra-atrial sensing from an atrial lead during atrial fibrillation. With sinus rhythm and with atrial flutter or non-physiologic atrial tachycardia as shown in FIGS. 2 and 3, there is little variation in the amplitude of the atrial signal from beat to beat. With atrial fibrillation, however, a considerable fluctuation is observed not only in cycle length from atrial-sense event to atrial-sense event, but also in the amplitude of the signal. This is attributable to the probabilistic nature and the chaotic pattern of the atrial wavelets that build up larger and smaller main rotors, which determine cycle length and amplitude. The asterisks above the atrial signals in FIG. 4 indicate which atrial-sense events fulfill the sensing criteria according to the sensing levels shown at the origin side of the Figure, so that an inappropriately high atrial rate is detected.

Figure 5:
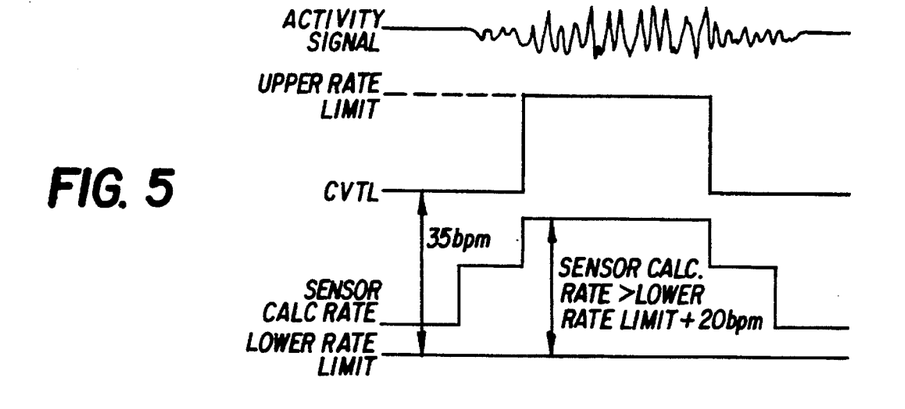
FIG. 5 is a chart illustrating the prior art principles of CVTL in a pacemaker.

FIG. 5 illustrates the principles of using a CVTL in pacemakers of the prior art. An accelerometer is used as a body motion/activity sensor. With the CVTL programmed "on", the paced rate in the ventricle jumps to the CVTL rate (e.g., 95 bpm, with a programmed lower rate limit of 60 bpm programmed in the pacemaker) when a high atrial rate is sensed without confirmation of accelerometer activity. An override of CVTL with the MPR is programmed "on" takes place when the sensor rate exceeds the programmed pacing rate by some preset amount such as 20 bpm, at which point 1:1 AV synchrony is restored up to the MPR.

Figure 6:
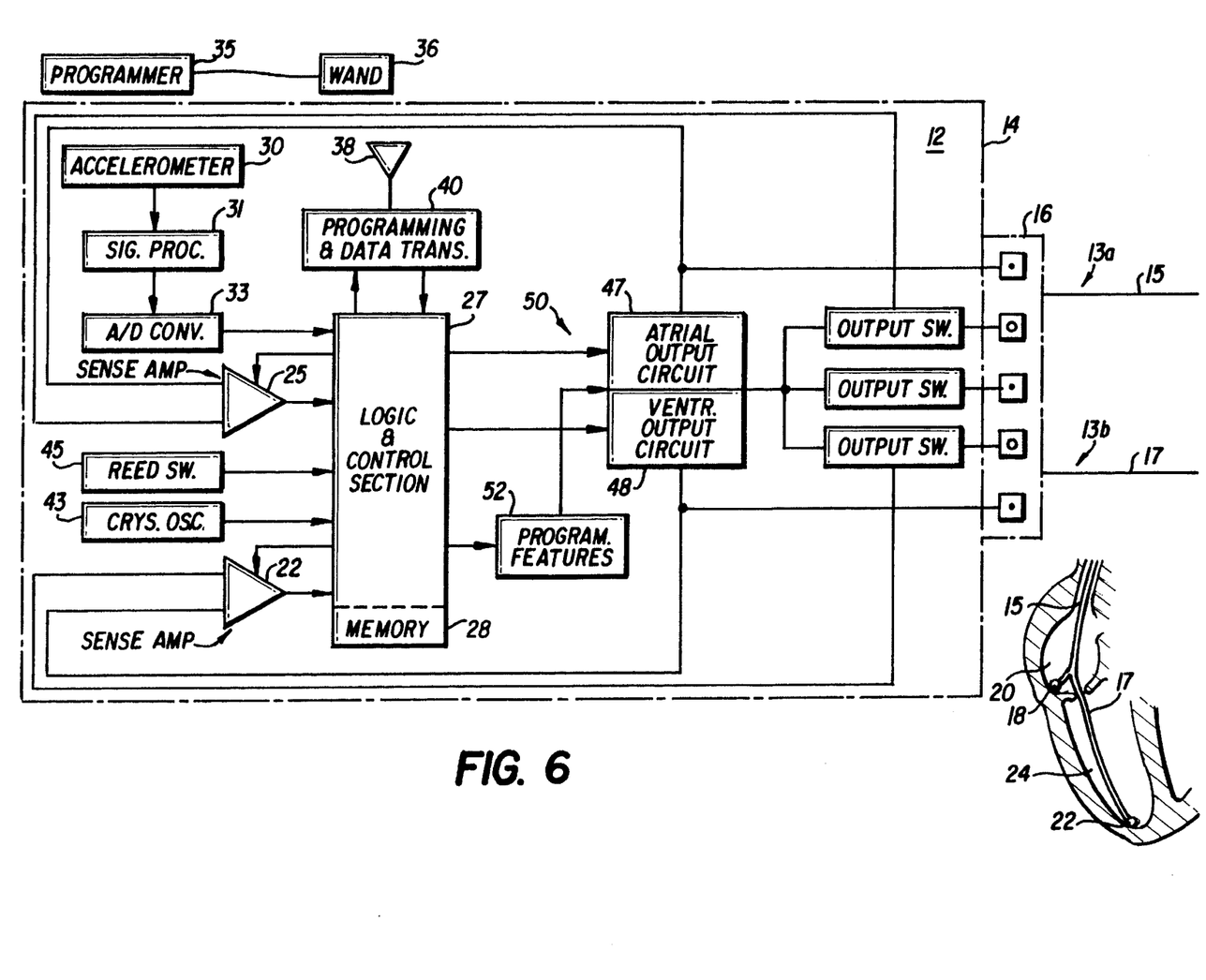
FIG. 6 is a block diagram of a body-implantable pacemaker generator embodying the principles of the present invention, together with external programmer, and showing the location of electrodes of a transvenous lead(s) in the atrium and ventricle.

Referring now to FIG. 6, a body-implantable pacemaker is implemented and implanted according to conventional principles, except as will be discussed presently, to provide dual-chamber (DDD) pacing. A multiprogrammable, rate-responsive pacemaker generator (cardiac pulse generator) 12 has a header on its case (enclosure, or can) 14 with an electrical connector 16 for connection to transvenous leads 13a and b with insulated atrial and ventricular electrical conductors 15, 17. The case is composed of metal (e.g., titanium), and serves to shield against electrical interference as well as to act as the indifferent electrode for sensing and pacing in the unipolar configuration. The transvenous leads are connected via the connector terminals and platinum feedthroughs to the electrical circuitry through the hermetically sealed enclosure of generator 12.

Before connection to the generator, the transvenous leads are implanted in the heart via the superior vena cava, for example. An electrode 18 at the distal end of transvenous lead conductor 15 is intended to be positioned in the right atrium 20 of the patient's heart 21 when transvenous lead 13a is fully implanted. Similarly, an electrode 22 at the distal end of conductor 17 is intended to be positioned in the right ventricle 24.

Each of the electrodes is disposed adjacent or in contact with excitable tissue of the myocardium of the respective heart chamber. The pacemaker generator 12 itself is implanted in a pocket surgically formed by separating the pectoral muscle fascia from the subcutaneous tissue in the patient's chest area, and then closing in layers after connecting the implanted transvenous leads to the generator. Determination of proper positioning, patient threshold, and sensitivity are achieved using known principles including a sensing threshold test, and a pacing threshold test using capture verification.

The generator circuit includes a pair of sense amplifiers 25, 26, for sensing in the atrium and ventricle, respectively. The amplifiers receive electrical signals detected by the respective electrodes 18, 22, and amplify the signals within the frequency range of cardiac depolarizations. The amplified signals are passed to a logic and control section 27 having associated memory 28.

An activity sensor comprising an accelerometer 30 senses body motions and passes this information to a signal processor 31. The signal processor filters and amplifies the activity signal received from the accelerometer (sometimes referred to herein simply as the "sensor activity"). Preferably, processor 31 provides low-pass filtering to restrict the frequency range of interest to an upper limit of about 4 Hertz (Hz), a range that tends to assure that the motions sensed by the accelerometer represent true physical exercise and not extraneous movement arising from other sources (noise) external or internal to the patient. The filter portion of the signal processor may be incorporated within a hybrid circuit structure that includes the accelerometer.

An analog-to-digital converter 33 receives the analog signal from the signal processor and converts it to the digital format to be used by logic and control section 27 to calculate the pacing rate. The logic and control section processes the signals from the sense amplifiers 25 and 26, using time-domain analysis to distinguish between valid cardiac signals and extraneous electrical interference ("noise") signals. The logic circuitry controls output circuit operation of the pulse generator according to the type of signal received from the sense amplifiers and the information stored in memory from an external programmer 35.

The logic circuitry also implements the programming commands received from programmer 35 via electromagnetic impulses from a programming wand 36 that are inductively coupled by an antenna coil 38 to a programming and data transmission section 40. The impulses contain the programming information, and are demodulated and stored to determine the programmable operating characteristics of the pulse generator. In addition, section 27 governs the data transmission system, which yields operating characteristics of the pulse generator and the lead system, as well as condition of the pulse generator's power supply (battery, not shown), and diagnostic data. Data transmission is activated via the programmer 35.

All timing functions of the pulse generator are controlled by a stable quartz crystal oscillator 43. A reed switch 45 allows certain limited functions and data of the pulse generator to be accessed and/or controlled from an external magnet (not shown).

Atrial and ventricular output circuits 47, 48 of output section 50 generate the stimulating pulses to be supplied to the respective chambers of the patient's heart, under the control (including the amplitude and timing of the pulses) of logic and control section 27.

In the preferred embodiment, the pulse generator is programmable in dual-chamber modes DDD, DDD-R, DDD+Hysteresis, VDD, or VDD-R. The DVTL (when activated, i.e., when programmed "on") is calculated each cycle according to the following formula:

$$DVTL \text{ interval} = \min \left\{ \frac{\frac{60{,}000}{VTL \text{ at rest}} - \left(\frac{60{,}000}{\text{pacing rate}} - \frac{60{,}000}{\text{sensor rate}}\right) \times \left(1 - \frac{1}{RLF}\right)}{\frac{60{,}000}{\text{last } DVTL \text{ used}} + \text{RATE DECAY}} \right\}$$

$$\text{where } RLF = \begin{bmatrix} \infty & \text{if } DVTL \text{ RATE LIMITING} = 0{:}1 \\ X & \text{if } DVTL \text{ RATE LIMITING} = 1{:}X \end{bmatrix}$$

The ventricular tracking limit for the patient at rest (no sensor 30 activity) is programmed as the VTLAR. This parameter is set by (i) a selected dual-chamber mode (e.g., DDD, DDD-R, DDD+Hysteresis, VDD, or VDD-R) of the pulse generator; and (ii) the requirement that (PPR+5 bpm)≦VTLAR≦MPR; and (iii) the VTL response to exercise=DVTL. For example, the VTLAR may range from a minimum of 80 bpm to a maximum not to exceed the MPR, programmable in step sizes of 5 bpm.

The DVTL rate limiting parameter is set by a selected dual-chamber mode, and the VTL response to exercise= DVTL. For example, the rate limiting parameter may have a programmed ratio of 1:1, 1:2, 1:4, or 1:8. The DVTL rate decay parameter may be set by those same factors, and programmed, for example, at a minimum of 2.5 ms, a maximum of 7.5 ms, and a step size of 2.5 ms.

Figure 7:
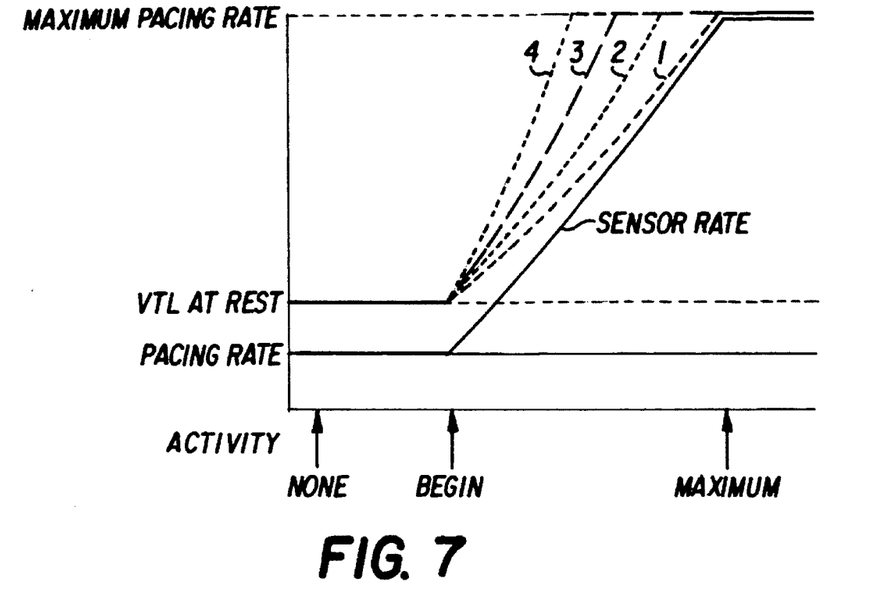
FIGS. 7 and 8 are graphs illustrating increasing DVTL with commencement and increase in physical activity (sensor activity), and decreasing DVTL with declining physical activity, respectively.
Figure 8:
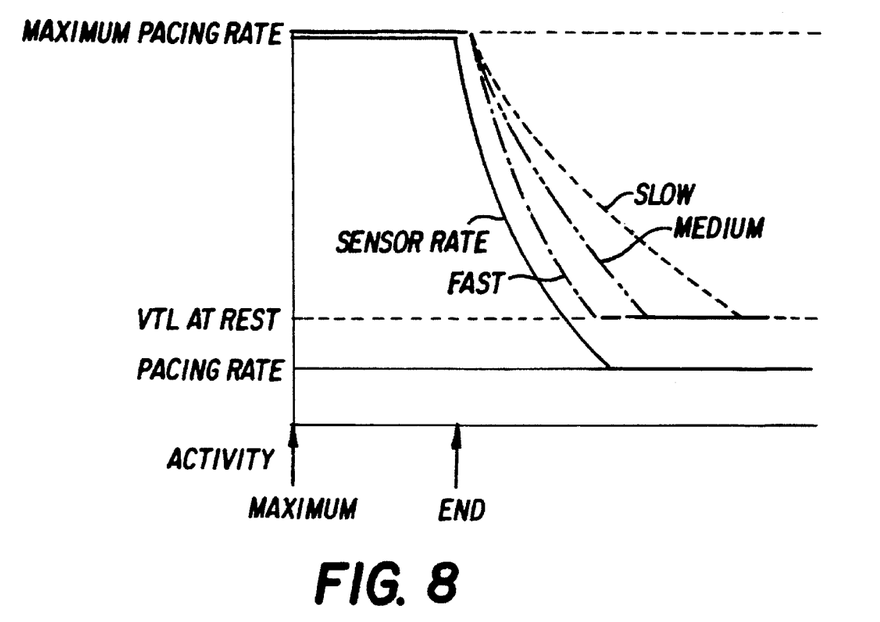

The device protects against inappropriate ventricular responses to high atrial rates not attributable to exercise (such as pacemaker mediated tachycardia, or atrial non-physiologic tachycardia) by implementing the DVTL based on the patient's activity level and on three programmable criteria, viz., the VTLAR, the DVTL rate limiting parameter or factor, and the DVTL rate decay parameter or factor. As observed above, the VTLAR is the pulse generator's lowest VTL and is in effect when the accelerometer indicates that the patient is at rest or performing only very minimal activity. As the accelerometer indicates a rise in patient activity, the DVTL increases in a curve corresponding to the programmed DVTL rate limiting factor, as shown in FIG. 7. As the accelerometer indicates a decrease in patient activity, the DVTL declines according to the programmed DVTL rate decay factor, as shown in FIG. 8.

The DVTL lower limit is restricted by the requirement that DVTL is never allowed to fall below the sensor (accelerometer) rate, and the DVTL upper limit is restricted by the requirement that it is never allowed to exceed the MPR.

The operational VTL is defined as follows. In dual-chamber tracking, the interval between any ventricular event (pace or sense) and the next ventricular pace should not be shorter than the interval corresponding to the operational VTL if the second ventricular pace followed a tracked atrial sense event.

The programming of the DVTL (activation), and the independent programming of VTLAR, MPR, and MSR (with VTLAR≦MPR≦MSR), together with programming the criteria for mode switching (dual-chamber to single-chamber, and reversion), is illustrated for the sake of convenience and clarity as a separate programmable features block 52 which establishes the multiple rate zones. In fact, however, this programming constitutes part of the functions performed using external programmer 35 to provide the stored information and the programming commands implemented by the logic and control section 27. The multiple rate zones resulting from a combination of the features of DVTL and automatic mode switching provide the principal advantages of pacing rate control in the dual-chamber pacemaker of the present invention, as will now be described with reference to FIGS. 9A and 9B.

Figure 9A:
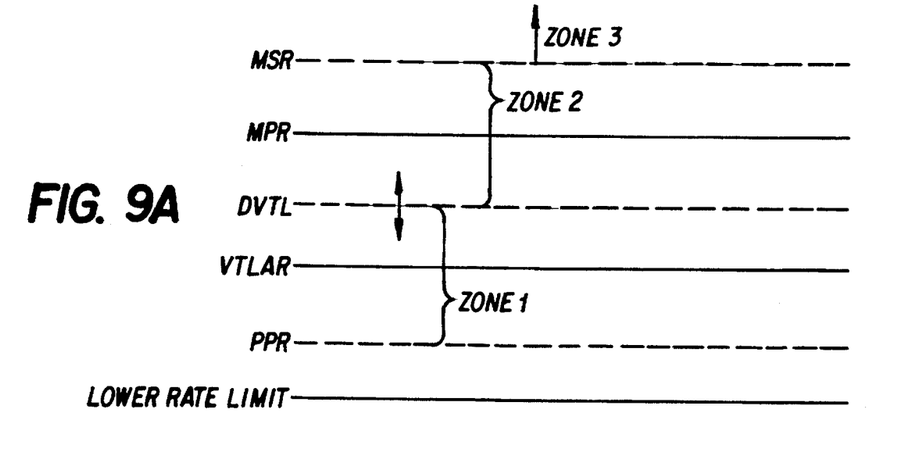
FIGS. 9A and 9B are diagrammatic representations illustrating the improved pacing rate control afforded by the multiple rate zones implementation of the present invention, FIG. 9A showing the three-zone analysis, and FIG. 9B the four-zone analysis.

Referring to the diagrammatic representation of FIG. 9A, the device (i.e., the pulse generator 12) is programmed with a lower rate limit as well as the PPR, VTLAR, MPR, and MSR. With no accelerometer activity, the PPR is in effect, being a nominal value deemed by the attending cardiologist to be an appropriate paced ventricular rate for the patient. In the Figure, the PPR is slightly higher than the lower rate limit of the device. For the sake of the instant analysis, three rate zones are present. A first zone (zone 1) extends from the PPR to the operational VTL determined, for any given cycle, from the calculation of DVTL. If the patient is resting, the operational VTL is the VTLAR. In this first rate zone, normal tracking takes place in which atrial activity within the zone is tracked in the ventricle on a 1:1 basis.

The second zone (zone 2) extends from the DVTL (operational VTL in any given cycle) to the MSR. Sensed atrial activity in this zone is tracked in the ventricle in Wenckebach fashion, and the ventricular pacing rate is limited by the DVTL which depends, at least in part, on sensor (accelerometer) activity. A third zone (zone 3) includes all rates above the MSR. Sensed atrial activity continues to be tracked in the ventricle in Wenckebach fashion until a programmed mode switch cycle criterion is met. In the preferred embodiment, the device mode switches from dual-chamber (e.g., DDD-R) to single-chamber (e.g., VVI-R), from among the specific modes programmed in the device for that purpose, whenever the sensed atrial rate exceeds the MSR in a manner that meets a specified (programmed) criterion. For example, the criterion my be a programmed number of cycles (ranging from 1 to 7) over which the sensed atrial rate exceeds the MSR. Once the device goes to the single-chamber mode it ignores all further sensor (physical/accelerometer-detected) activity. And the device reverts to the dual-chamber (DDD-R) mode whenever the sensed atrial rate falls below the MSR according to another criterion (e.g., for one cycle).

Figure 9B:
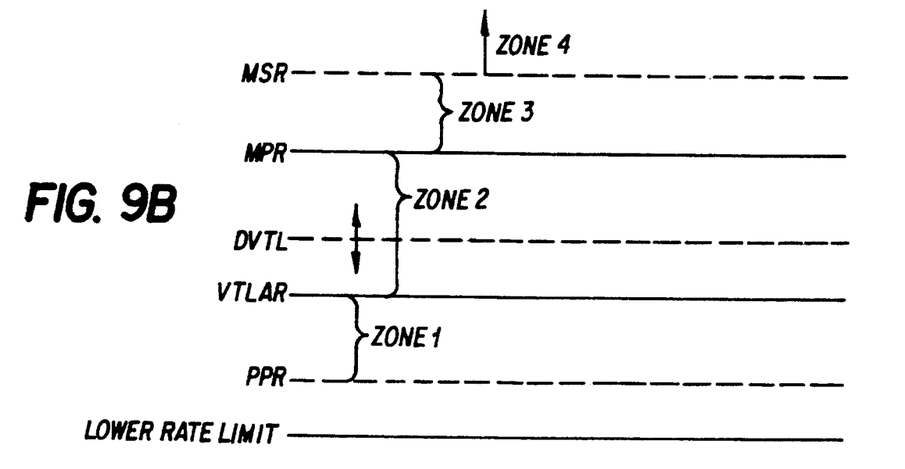

In FIG. 9B, four rate zones are present. In a first zone (zone 1), extending from the PPR to the VTLAR, atrial activity is always tracked in the ventricle on a 1:1 basis. In a second zone (zone 2) that extends from the VTLAR to the MPR, atrial activity is tracked in the ventricle either on a 1:1 basis or in Wenckebach fashion depending on physical activity levels (sensor activity). In contrast to the "always tracked" ventricular paced response in zone 1, the response in zone 2 may be characterized as "possibly tracked."

In a third zone (zone 3) that extends from the MPR to the MSR, the sensed atrial activity is tracked in the ventricle in Wenckebach fashion, with the ventricular pacing rate limited by the DVTL. This may be characterized as "always Wenckebach tracked." Zone 3 may be programmed away by setting the MPR equal to the MSR. If that were done, the four-zone analysis would be at least substantially the same as the three-zone analysis discussed above, with zones 2 and 3 of the former combined to be the same as zone 2 of the latter. Zone 4 and its analysis are identical to those of zone 3 of the three-zone version above.

It will be observed, then, that the invention provides improved pacing rate control that tends to mirror the rate changes that are observed as physiologically appropriate in the cardiovascular system of a normal, healthy subject.

Although certain preferred embodiments and methods have been disclosed herein, it will be appreciated that those skilled in the art to which the invention pertains will recognize that variations and modifications may be implemented from a consideration of the foregoing description, without departing from the spirit and scope of the invention. Accordingly, it is intended that the invention shall be limited only as required by the appended claims and the rules and principles of applicable law.

What is claimed is:

1. An implantable, programmable, dual-chamber, rate-adaptive cardiac pulse generator for sensing atrial activity of the patient's heart and for tracking the sensed atrial activity as a pacing rate for the ventricle within programmable lower and upper rate limits, the upper rate limit being a programmable maximum pacing rate for the ventricle, said pulse generator comprising sensor means for developing a rate control signal representative of the status of physical activity of the patient, means responsive to said sensor means for providing a ventricular tracking limit between said lower and upper rate limits that establishes a maximum ventricular pacing rate ranging upward from a resting ventricular tracking limit whenever the sensor means rate control signal is indicative of no physical activity, and control means further responsive to said sensor means for dynamically varying the ventricular tracking limit directly with the sensor means rate control signal indicative of physical activity to allow the sensed atrial activity to be tracked in the ventricle as a dynamic ventricular tracking limit constituting a new operational limit for ventricular response consistent with current level of physical activity indicated by the sensor means up to the upper rate limit constituting said maximum pacing rate for the ventricle.

2. The pulse generator of claim 1, wherein said control means includes means for calculating dynamic ventricular tracking limit in each cardiac cycle.

3. The pulse generator of claim 1, further including programming means for establishing a programmable mode switch rate exceeding said maximum pacing rate to effect a transition from a dual-chamber mode to a single-chamber mode of the pulse generator whenever the sensed atrial activity rate exceeds the programmed mode switch rate for a predetermined interval, without regard to physical activity indicated by the sensor means rate control signal.

4. The pulse generator of claim 3, wherein said programming means further establishes said programmable mode switch rate to effect a reversion from said single-chamber mode to said dual-chamber mode whenever the sensed atrial activity rate falls below the programmed mode switch rate for a predetermined interval, to return control of the ventricular pacing rate at least partly to the sensor means rate control signal.

5. The pulse generator of claim 4, wherein said programming means includes means for establishing a plurality of rate zones for control of the ventricular pacing rate, said rate zones including a first zone ranging from a rate exceeding said lower rate limit to an operational limit defined by the dynamic ventricular tracking limit for a given cardiac cycle, a second zone ranging from the last-named operational limit to the programmed mode switch rate, and a third zone having a lower boundary defined by a sensed atrial activity rate equal to the programmed mode switch rate.

6. The pulse generator of claim 1, wherein said sensor means comprises an accelerometer.

7. The pulse generator of claim 6, wherein said accelerometer is contained within an enclosure that houses the pulse generator.

8. A programmable dual-chamber artificial cardiac pacemaker, comprising means for sensing atrial activity, means responsive to sensed atrial activity for normally tracking thereof to pace ventricular activity accordingly, means for sensing physical exercise by a patient when the pacemaker is implanted in the patient and for generating a rate control signal indicative of extent of the sensed physical exercise, and means for programming the pacemaker for ventricular pacing rate control in multiple rate zones bounded by rate limits including (i) a ventricular tracking limit (VTL) that varies dynamically with sensed physical exercise and (ii) a higher mode switch rate, so that the ventricular pacing rate tracks the sensed atrial activity on a 1:1 basis for atrial rates below the dynamic VTL (DVTL) during a predetermined interval of time for which the DVTL applies and tracks the sensed atrial activity in Wenckebach behavior for atrial rates above the DVTL up to the mode switch rate with the ventricular pacing rate limited by the DVTL.

9. The pacemaker of claim 8, wherein said programming means sets the mode switch rate to effect a switch from dual-chamber to single-chamber mode when the sensed rate of atrial activity exceeds the mode switch rate for a predetermined number of cardiac cycles, in which the ventricular pacing rate is controlled solely by sensed spontaneous ventricular activity without regard to the DVTL or sensed physical exercise, and to effect a reversion to the dual-chamber mode when the sensed rate of atrial activity drops below the mode switch rate for a predetermined number of cardiac cycles, in which the ventricular pacing rate is controlled according to the respective one of said multiple rate zones in which the atrial activity rate is present.

10. The pacemaker of claim 9, wherein said physical exercise-sensing means comprises a physical activity sensor.

11. A device-implemented method of controlling ventricular pacing rate in a programmable dual-chamber artificial cardiac pacemaker, the method comprising the steps of sensing atrial activity, normally pacing ventricular activity tracked to the sensed atrial rate, sensing physical exercise by a patient when the pacemaker is implanted in the patient and generating a rate control signal indicative of extent of the sensed physical exercise, and programming the pacemaker for ventricular pacing rate control in multiple rate zones bounded by rate limits including (i) a ventricular tracking limit (VTL) that varies dynamically with sensed physical exercise and (ii) a higher mode switch rate, so that the ventricular pacing rate tracks the sensed atrial activity on a 1:1 basis for atrial rates below the dynamic VTL (DVTL) during a predetermined interval of time for which the DVTL applies and tracks the sensed atrial activity in Wenckebach behavior for atrial rates above the DVTL up to the mode switch rate with the ventricular pacing rate limited by the DVTL.

12. The device-implemented method of claim 11, including setting the mode switch rate to effect a switch from dual-chamber to single-chamber mode when the sensed rate of atrial activity exceeds the mode switch rate for a predetermined number of cardiac cycles, in which the ventricular pacing rate is controlled solely by sensed spontaneous ventricular activity without regard to the DVTL or sensed physical exercise, and to effect a reversion to the dual-chamber mode when the sensed rate of atrial activity drops below the mode switch rate for a predetermined number of cardiac cycles, in which the ventricular pacing rate is controlled according to the respective one of said multiple rate zones in which the atrial activity rate is present.

* * * * *